United States Patent
Mujallid

(10) Patent No.: US 10,136,650 B2
(45) Date of Patent: Nov. 27, 2018

(54) REPELLANT COMPOSITION FOR AN ANTI-REPELLANT FABRIC AND A DEVICE TO EVALUATE THE SAME

(71) Applicant: Umm-Al-Qura University, Makkah (SA)

(72) Inventor: Rasha Sameer Mohammad Mujallid, Makkah (SA)

(73) Assignee: Umm-Al-Qura University, Makkah (SA)

( * ) Notice: Subject to any disclaimer, the term of this patent is extended or adjusted under 35 U.S.C. 154(b) by 54 days.

(21) Appl. No.: 14/661,784

(22) Filed: Mar. 18, 2015

(65) Prior Publication Data

US 2016/0270408 A1   Sep. 22, 2016

(51) Int. Cl.
*A01N 65/26*   (2009.01)
*A01M 1/02*   (2006.01)
*D06M 15/05*   (2006.01)

(52) U.S. Cl.
CPC ............ *A01N 65/26* (2013.01); *A01M 1/026* (2013.01); *D06M 15/05* (2013.01); *D06M 2200/00* (2013.01)

(58) Field of Classification Search
CPC ..... A01N 65/26; A01M 1/026; A01M 1/2055; A01M 1/2005
See application file for complete search history.

(56) References Cited

U.S. PATENT DOCUMENTS

| | | | | |
|---|---|---|---|---|
| 8,402,383 B1* | 3/2013 | Fisher | ............. | G06F 9/542 715/777 |
| 8,808,721 B2* | 8/2014 | Banfield | ............. | A01M 1/026 424/406 |
| 8,832,994 B2* | 9/2014 | Tolley | ............. | A01M 1/026 43/131 |
| 9,185,898 B2* | 11/2015 | McIntyre | ............. | A01M 1/2055 |
| 9,210,924 B1* | 12/2015 | Terrell | ............. | A01M 23/26 |
| 2013/0298446 A1* | 11/2013 | Rubel | ............. | A01M 1/2055 43/132.1 |
| 2013/0303574 A1* | 11/2013 | Gaugler | ............. | A01N 25/00 514/345 |
| 2014/0173971 A1* | 6/2014 | Boyd | ............. | A01M 29/12 43/125 |

\* cited by examiner

*Primary Examiner* — Monica L Williams
(74) *Attorney, Agent, or Firm* — Geeta Kadambi; Riddhi IP LLC

(57) ABSTRACT

The present disclosure relates to an anti-repellant compound and a method of using the same n a material to give them anti-repellant properties. Further, the disclosure also relates to a device to evaluate anti-repellant property of a fabric or any other material. The device calculate the average distance crossing by an insect or other parasites and then calculate the percentage of resistant fabric. Thus, giving an idea on how effective the fabric is for its anti-repellant properties.

5 Claims, 4 Drawing Sheets

REPELLANT COMPOSITION FOR AN ANTI-REPELLANT FABRIC AND A DEVICE TO EVALUATE THE SAME

FIELD OF TECHNOLOGY

This disclosure generally relates to an anti-repellant composition which may be used to produce any anti-repellant material. Further, the disclosure relates to a device for evaluating anti-repellant properties of any material including fabrics.

BACKGROUND

Direct or indirect attacks from insects are always annoying, troublesome, dangerous and sometimes life threatening. Insects, bugs or mosquitoes can transmit a number of serious diseases such as dengue fever, tick-borne encephalities, barbesiosis, lyne disease, malaria, plague among others. Workers, tourists, explorers or other beings exposed to such conditions and environments where they are constantly exposed to bugs, ticks, insects or mosquitoes need to take special protective measures for themselves. They always have to take special clothing, equipments and other precautions with them to work in such conditions.

SUMMARY

The present disclosure relates to an anti-repellant compound. Further, the present disclosure relates to a device to evaluate anti-repellant property of a material.

In one embodiment, the present disclosure relates to an anti-repellant compound. In another embodiment, the anti-repellant compound may be used for finishing and treatment of a material and thus making it as anti-repellant material. Further, the anti-repellant compound may be used for finishing and treatment of a fabric and thus making an anti-repellant fabric.

In one embodiment, the anti-repellant compound comprise of extract from green neem's leaves. Thus, a process of preparing an extract comprise of placing more than one neem leaf in water; adding alcohol into the water; and collecting a neem extract.

The compound was extracted from neem's leaves by placing leaves in water; adding alcohol into water to activate the extraction and collecting the extract. In another embodiment, the anti-repellant compound comprise of extract from dry neem's leaves following the same procedure.

In one embodiment, a fabric or a material, when synthesized was then given a final treatment and finishing with the disclosed anti-repellant compound. In another embodiment, the final treatment and finishing help in adding anti-repellant features to the fabric or material synthesized and thus can be used for making clothing, shoes, tents, fabric or other anti-repellant equipments.

In one embodiment, the present disclosure relates to a device to evaluate anti-repellant property of a fabric or a material. In another embodiment, the device as disclosed, measures the effectiveness of the fabric or material against various mosquitoes, tics, insects, bugs or other parasites.

The device as disclosed comprise of a long tube; a box; a cover for box; a cover for catch sample; a zero point indicator; a scale; a cover for moistened cotton; and a cover for insect entrance wherein the device calculate the average distance crossed by a parasite followed by calculating the percentage of resistance by the fabric or the material with anti-repellant property.

Thus, the present disclosure relates to an anti-repellant composition, use of the anti-repellant composition to make an anti-repellant material and a device to measure the effectiveness of anti-repellant compound.

Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

DETAILED DESCRIPTION

Figure 1:
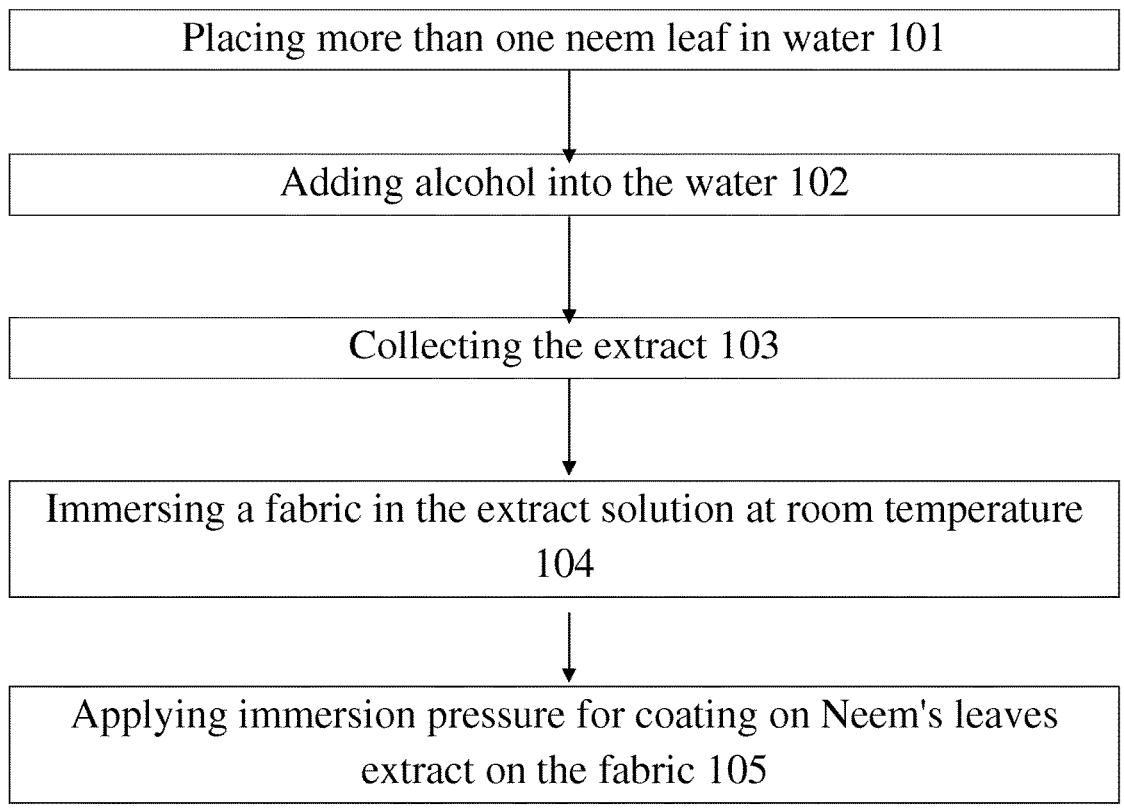
FIG. 1 shows showing synthesis of disclosed anti-repellant composition and its use on fabric.

Neem's is considered a weed in many areas, including some parts of the Middle East, and most of desert Africa including West Africa and Indian Ocean states (Steve Csurhes, 2008). Neem's leaves are dried in India, Pakistan and placed in cupboards to prevent insects eating the clothes and also while storing rice (Anna Horsbrugh Porter, 2006).

However, insufficient research has been done to assess the purported benefits of neem's (Tamilndu.com, 2012). Neem's is a key ingredient in non-pesticidal management (NPM), providing a natural alternative to synthetic pesticides. Neem's seeds are ground into a powder that is soaked overnight in water and sprayed onto the crop. To be effective, it is necessary to apply repeatedly, at least every ten days. Neem's does not directly kill insects on the crop. It acts as an anti-feedant, repellent, and egg-laying deterrent, protecting the crop from damage (Schmutterer et al, 1986). The insects starve and die within a few days. neem's also suppresses the hatching of pest insects from their eggs. Neem's cake is often sold as a fertilizer (Neem newsletter, 1988). Neem's also acts as a bird repellent: wherein neem's leaf boiled in water can be used as a very cost effective bird repellent, especially for sparrows (Saxena, 1989).

U.S. Pat. No. 4,671,960 by Thielen, et al. titled "Herbal repellent composition", discloses a natural flea repellent herbal composition using the dry, finely chopped solids of pennyroyal, eucalyptus, and camomile with a small amount of oil of pennyroyal, eucalyptus, and citronella for increased effect, a method for production of a material receptical used as a pet collar. An apparatus for the insertion of the natural flea repellent herbal composition within the material receptical.

U.S. Pat. No. 7,575,765 by Hughes titled "Topical insect repellent", discloses an "all-natural" topical insect repellent formulation having a long shelf life. The formulation includes a carrier base of fractionated coconut oil, and an effective amount of at least one essential oil with insect repellent capabilities. As active ingredients the essential oils cedarwood oil, citronella oil and lemongrass oil may be employed, with a total concentration of these active ingredients of 15.3% by weight.

U.S. Pat. No. 7,144,591 by Bencsits titled "Composition containing citronella java oil and use thereof for repelling insects", discloses a composition comprising a specific ethereal oil, which may be used as insect repellent.

U.S. Pat. No. 5,776,477 by Ryder titled "Organic insect repellent", discloses An environmentally safe, topical pest repellent is described. The repellent comprises a variable mixture of natural ingredients including pennyroyal herb, tansy herb, calendula, citronella, pyrethrin and aloe vera. A method is provided to produce tinctures which are combined to form a composition for application to skin of animals such as horses to repel pests such as flies, mosquitoes, ticks, and other insects. The composition may be applied to animals by spraying or other suitable devices and carriers.

U.S. Pat. No. 5,372,817 by Locke et al titled "Insecticidal compositions derived from neem's oil and neem's wax fractions", discloses a novel insecticide compositions prepared from neem's seeds are disclosed. Two distinct neem's derived insecticides obtained non-polar, hydrophobic solvent neem's seed extracts which are substantially free of azadirachtin, by removing the hydrophobic solvent and cooling the resulting neem's oil to separate a semi-solid neem's wax fraction and a clarified neem's oil fraction.

The present disclosure relates to an anti-repellant composition which can be used as a coating or as a treatment over a material to make it function as an anti-repellant. The composition as disclosed can be used as treatment for any synthesized material or a fabric to make anti-repellant fabric, clothing, tents, ropes or other material. As the textile and fabric industry is expanding and trying to add a number of features to the fabric to make it more useful and different and extreme conditions. Manufacturers are trying to manufacture anti-repellant fabric which is easy to synthesize, durable, soft, non-irritant and can be designed in different shapes and sizes with ease.

Thus, the present disclosure relates to an anti-repellent fabric to mosquitoes and more particularly, to natural mosquitoes and other parasites. More importantly, the composition as disclosed can be used for making anti-repellant fabric which is non-irritating and harmless.

The composition as disclosed comprise of extract of green and dry neem's leaves, Preparation of Compound Extracted from Neem's Leaves A Compound was extracted from neem's leaves by placing leaves in water. The active compound from the leaves has a low solubility in water, so 20-200 grams of green and dry leaves were used for every liter of water. One may also use 50 grams of green and dry leaves for every liter of water. The active compound of neem has low solubility, the use of solvents may increase the concentration of the compounds in the water and therefore so alcohol may be used to active the compounds of the extracted from the neem's leaves (Feuerhake, 1983).

The compound extracted from neem's leaves by using alcohol was found to have highest concentration which may be fifty times rather than if the extraction is done by using water only. For the present application, ethanol was used for extraction of neem leaves compound. Ethanol has no effect on the product properties and also gets evaporated (Feuerhake et al, 1982) once the compound is used as a protective layer over a material to make it anti-repellant.

The solution of treatment for fabric was prepared from the extracted of green and dry neem's leaves. It was noticed that the compound extracted from green neem's leaves had a color clearer than the same extracted from dry neem's leaves, also the smell of green leaves was good.

Thus, as shown in FIG. 1, process of preparing an extract comprise of placing more than one neem leaf in water; adding alcohol into the water; collecting a neem extract; immersing a material in the extract solution at room temperature; applying immersion pressure for coating on Neem's leaves extract on the material.

Treatment of Fabric with the Extracted Compound

Figure 2:
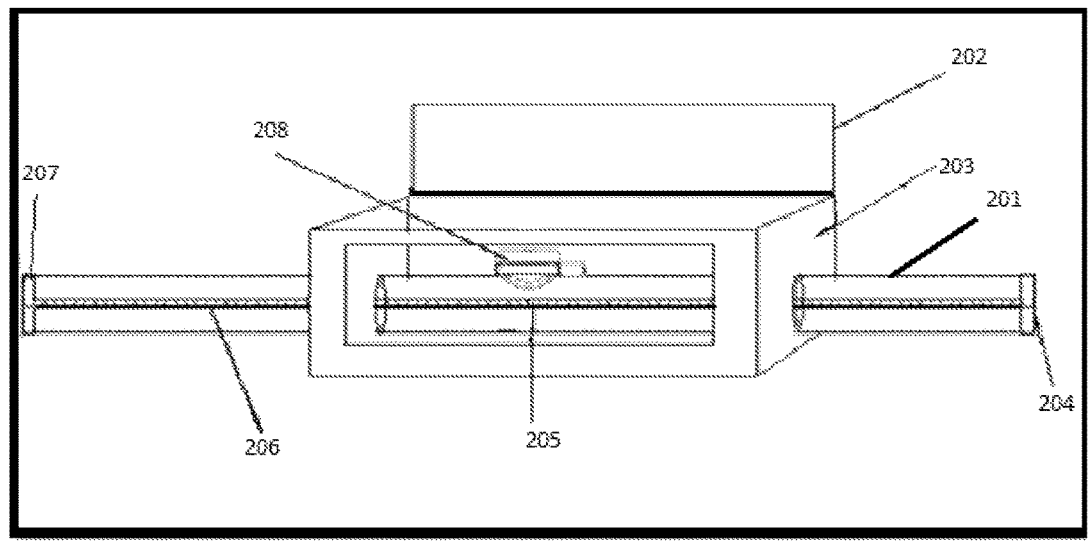
FIG. 2 shows parts of the disclosed device.

To treat the fabric with extracted compound from green and dry neem's leaves, the fabrics were immersed in an extracted solution at room temperature and immersion pressure can be adjusted to add 1-10% or 2-5% of the extract compound of neem's leaves to fabric (R P. Singh et al, 1988). As shown in FIG. 2, the device as disclosed comprise of a long tube 201; a box 203; a cover for box 202; a cover for catch sample 204; a zero point indicator 205; a scale 206; a cover for moistened cotton 207; a cover for insect entrance 208. The tube as shown may be made up of acrylic or other suitable material. The length of the tube may vary from 50-200 cm preferable 100 cm.

Further, the box as shown may be made up of wooden or other suitable material or of the same material as of tube. The box may be 48 cm×20 cm×20 cm in dimension or may be of other suitable length. The tube as disclosed has two opposite holes from both sides and thus the tube is through going. Thus, the tube has a left-side opening and a right-side opening. The device as disclosed calculate a percentage of resistant fabric for a parasite.

Figure 3:
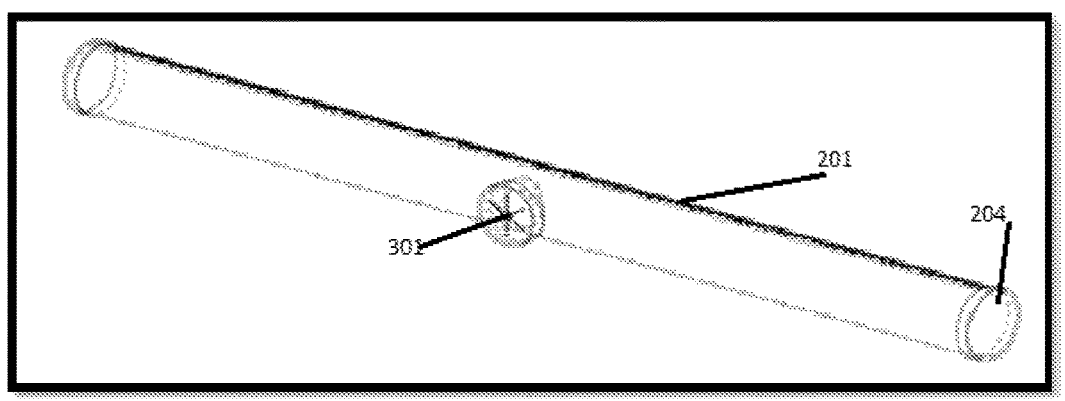
FIG. 3 shows a side view of the disclosed device.

FIG. 3 shows a side view of the disclosed device wherein the acrylic tube 201 has a zero point indicator in the middle. There is also an entrance 301 in the middle of the tube. The entrance in the middle is for an introduction of an insect. To introduce an insect, the lid cover if opened to enter the insect along with sir and is closed following the introduction.

Figure 4:
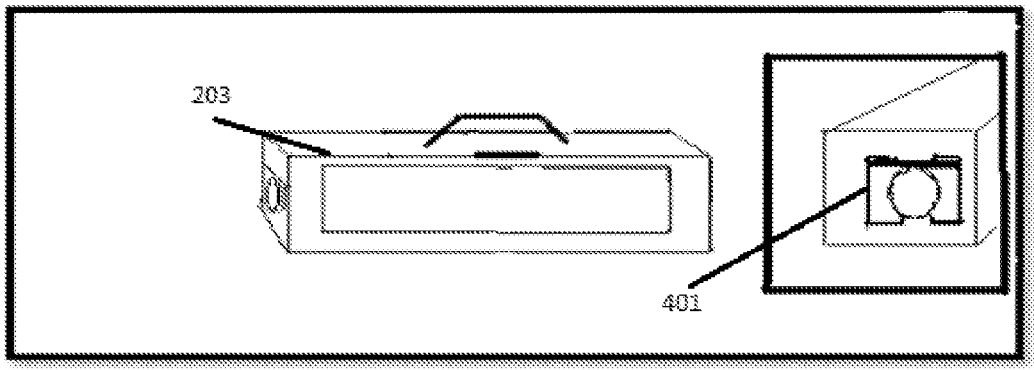
FIG. 4 shows the box as in the disclosed device.

FIG. 4 shows the details of the box of the disclosed device. As shown in FIG. 4, the box 203 has a sliding door 401 on the left side of the box. The sliding door allows one to remove the tube with ease. This also helps if easy assembling and dis-assembling of the device and also to clean the device which is required for a better performance of the device.

Test of the Devise to Assess Anti-Repellant Property of a Material

There are some standards for evaluating the effect the treated fabric against insects, as AATCC Test Method 24-1999, this is biological test method for evaluating the resistance of textiles that contain wool or other susceptible fibers to webbing clothes moths and to carpet beetles.

This test method used to measure the resistance of the treated and untreated textile to insect attack, and measure quantitatively the amount of feeding on the test specimen by the specified number and type of insects for a prescribed time under controlled conditions of temperature and humidity (AATCC Test Method 24-1999).

Three fabric samples were prepared, one is control sample without treatment, second sample treated with green neem's leaves and the third treated with dry neem's leaves. The tested fabric sample is placed in the test device from the right side of the tube, and the other side of tube, moistened cotton is placed (501). The mosquitoes are inserted from the middle of tube, then the tube and box were closed, the light was closed about 20 minutes, then the box opened again.

Figure 5:
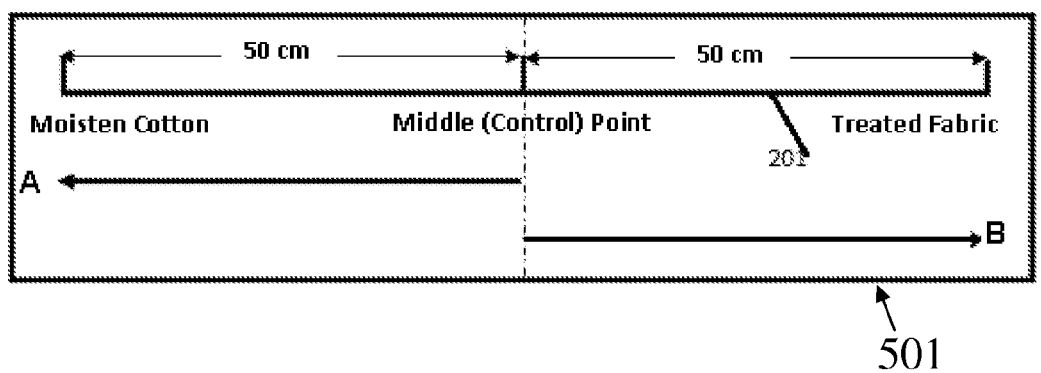
FIG. 5 shows evaluation of a treated fabric by the disclosed device.

The treated fabric as is one of the application of this invention, which can be an outer wear such as men's wear, women's wear and kid's wear among others. FIG. 5 shows the positions of tested fabric and moisten cotton. The sample of treated fabric was placed in the right side of the tube, and in other side (left) a piece of moisten cotton moistened was placed, then 10 of mosquitoes per test were inserted from the entry in the center of the tube which has a cover, then the lid or cover was closed.

Figure 6:
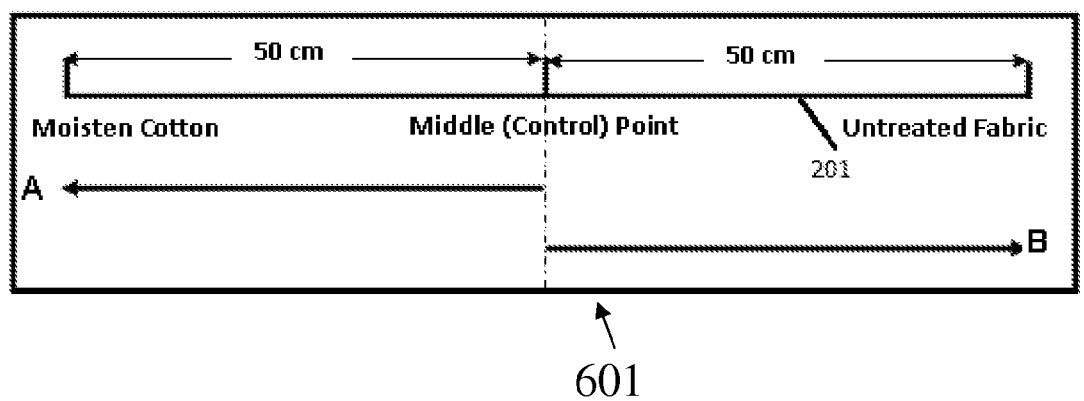
FIG. 6 shows evaluation of an untreated fabric by the disclosed device.

Then the box was closed and light was off for about 20 minutes. Following this, the box was opened again and numbers of mosquitoes which fled more than 50 cm from the middle of the tube towards the treated fabric in right direction or which fled in direction of moisten cotton left side were recorded. The test was repeated for treated fabric with green neem leaves and for treated fabric with dry neem leaves, and for untreated fabric (601; FIG. 6).

If the mosquitoes fled in direction of moisten cotton on the left side, because of the effect of fabric treated with green and dry neem's leaves, then the average of the far side from treated fabric was measured for every mosquito, and evaluates the repellent as the far side related to 10 cm.

Repellent (%)=Avg. of far side distance from treated fabric/100

If the mosquitoes fled in direction of untreated fabric (control fabric) to the right side, then the average of the near side from untreated fabric was measured for every mosquito, and evaluates the attraction as the near side related to constant 100 cm.

Attraction (%)=Avg. of near side distance from untreated fabric/100

| Tested sample | Distance of repellent the Mosquitoes (cm) | Repellent in Percentage (%) | Percentage of attraction of Mosquitoes |
|---|---|---|---|
| Untreated sample | Zero | Zero | 100% |

Tables 1 shows the effect of untreated (control) on repellent mosquitoes.

As shown in table 1, the number and percentage of mosquitoes which were rippled far away from the control fabric (untreated) and flied 25 cm or more in left direction, was counted and recorded. We can see that all mosquitoes fled in the direction of untreated sample, it means that the untreated fabric attracts mosquitoes in 100%. and it is not repellent.

| Tested sample | Distance of repellent the Mosquitoes (cm) | Repellent in Percentage (%) | Percentage of attraction of Mosquitoes |
|---|---|---|---|
| Treated with greenneem's leaves | 40 | 80% | 20% |

Tables 2 shows the effect of treated fabric with green neem's leaves as repellent mosquitoes.

As shown in table 2, the number and percentage of mosquitoes which were rippled far away from the treated fabric with green neem's leaves and flied in left direction 25 cm or more was counted and recorded. The mosquitoes were unable to fly towards the treated fabric with green neem's leaves, the distance from middle (control) point to treated fabric was zero, the mosquitoes flied towards moisten cotton in other direction, the flying distance of mosquitoes from middle (control) point to moisten cotton was 40 cm, it means that the percentage of repellent=80%.

| Tested sample | Distance of repellent the Mosquitoes (cm) | Repellent in Percentage (%) | Percentage of attraction of Mosquitoes |
|---|---|---|---|
| Treated with dryneem's leaves | 30 | 60% | 40% |

Tables (3) shows the effect of treated fabric with dry neem's leaves as repellent mosquitoes.

As shown in table 3, the number and percentage of mosquitoes which were rippled far away from the treated fabric with dry neem's leaves and flied 25 cm or more in left direction was counted and recorded. The mosquitoes were unable to fly towards the treated fabric with dry neem's leaves, the distance from middle (control) point to treated fabric was zero, the mosquitoes flied towards moisten cotton in other direction, the flying distance of mosquitoes from middle (control) point to moisten cotton was 30 cm, it means that the percentage of repellent=60%.

Thus as shown in the above studies, the treated fabric with green neem's leaves is more effective than the treated fabric with dry neem's leaves.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

REFERENCES

Pest Plant Risk Assessment, Neem Tree, *Azadirachta indica*. Biosecurity Queensland. 2008. Retrieved 24 Jan. 2014.
Anna Horsbrugh Porter (17 Apr. 2006). "Neem: India's tree of life". BBC News.
"Neem". Tamilnadu.com. 6 Dec. 2012.
Schmutterer et al., vol. 1: The Neem Tree, "Effects of Neem on Pests of Vegetables and Fruit Trees", pp. 69-83 (1986).
Neem Newsletter, (October-December 1988).
Saxena, Insecticides of Plant Origin, Ch. 9, ("Insecticides from Neem"), pp. 110-135 (1989).
Feuerhake, "Effectiveness and Selectivity of Technical Solvents for the Extraction of Neem Seed Components with Insecticidal Activity", Proc. 2nd Int. Neem Conf., pp. 103-114 (1983).
Feuerhake et al., "Simple Methods for the Extraction and Formulation of Neem Seeds and Their Effect on Various Insect Pests", Journal of Plant Diseases and Protection, 89(12), pp. 737-747 (1982).
R P. Singh et al., "Activity of Neem (*Azadirachta indica* A Juss) Seed Kernel Extracts against the Mustard Aphid, *Lipaphis erysimi*", Phytoparasitica, 16(3), 225-230 (1988).
AATCC Test Method 24-1999, "Insects Resistance of Textiles to".

What is claimed is:

1. A device to evaluate anti-repellant property of a material, comprising:
    a long tube, wherein the long tube is cylindrical in shape with a first open end on one side of the long tube and a second open end on the opposite side of the long tube such that the long tube is compartmentalized with one compartment holding a moisten cotton and another compartment holding an anti-repellant treated material;
    a box to house the long tube, wherein the box has a sliding door on one end of the box such that the door can slide open and close to assemble and disassemble the long tube;
    a cover for the box, wherein the cover for the box is on the upper end of the box and the cover opens and closes for its use;

a cover for a catch sample, wherein the cover for the catch sample closes the opening on the end of the long tube holding the anti-repellant treated material;

a zero point indicator, wherein the zero point indicator is at the middle point of the long tube and divides the long tube into compartments;

a scale, wherein the scale runs through the body of the long tube; and a cover for moistened cotton, wherein the cover for the moistened cotton closes the opening on the end of the long tube holding the moistened cotton wherein the device measures the effectiveness of the material as an anti-repellant.

2. The device of claim 1, wherein the device further comprises:

a cover for insect entrance, wherein an insect or other parasite can enter the device through the insect entrance when the cover is in open position and once the insect or other parasite is inside the device, the cover for the insect entrance is turned into a close position to evaluate anti-repellant property of the material.

3. A method of measuring the effectiveness of the anti-repellant material using the device of claim 2, comprising the steps of:

positioning a moisten cotton on one side of the long tube;

positioning a material to be tested as anti-repellant on the opposite side of the long tube, opposite to the position of moisten cotton;

inserting insects into the device through the opening of the cover for insects entrance;

closing the device from all sides;

switching off lights around the device for few minutes;

switching on the lights around the device after few minutes;

opening the device to calculate the number of insects moved towards the moisten cotton, the material being tested as anti-repellant in the middle portion of the long tube;

calculating the number of insects moved towards the direction of the material to be tested as anti-repellant and insects moved towards the direction of the moisten cotton; and measuring the distance travelled by the insect using the scale running through the long tube, from the position of the cover for insects entrance towards the moisten cotton and material tested as anti-repellant;

wherein the average of the number of insects and the distance travelled by insects towards moisten cotton or material provides the measure for effectiveness of an anti-repellant material such that if more insects travel towards the material, the material is not effective as an anti-repellant whereas if less insects travel towards the material, the material is an effective anti-repellant.

4. The device of claim 1, wherein the material is a fabric.

5. The device of claim 1, wherein the material is treated with an anti-repellant compound comprising neem leaf extract.

* * * * *